United States Patent [19]

Vellucci

[11] 4,294,894
[45] Oct. 13, 1981

[54] TRANSPARENT TOOTHPASTE HAVING A MEDICINAL ACTION AND PROCESS FOR ITS PRODUCTION

[75] Inventor: Enzo Vellucci, Rome, Italy

[73] Assignee: E. R. Squibb & Sons, Inc., Princeton, N.J.

[21] Appl. No.: 121,933

[22] Filed: Feb. 15, 1980

Related U.S. Application Data

[63] Continuation of Ser. No. 3,565, Jan. 15, 1979, abandoned.

[51] Int. Cl.³ .............................. A61K 9/16; A61K 9/18; A61K 7/22; B65D 81/24
[52] U.S. Cl. ........................................ 424/49; 424/52; 424/54; 206/524.4; 423/335
[58] Field of Search ................. 424/49–58; 206/524.4

[56] References Cited

U.S. PATENT DOCUMENTS

| | | | |
|---|---|---|---|
| 1,968,858 | 8/1934 | Sheffield | 424/49 |
| 2,658,851 | 11/1953 | Brandenberger | 424/49 |
| 2,994,642 | 8/1961 | Bossard | 424/49 |
| 3,538,230 | 11/1970 | Pader et al. | 424/52 |
| 3,842,167 | 10/1974 | Block et al. | 424/49 |
| 3,939,262 | 2/1976 | Kim | 424/52 |
| 4,122,160 | 10/1978 | Wason | 424/49 |
| 4,122,161 | 10/1978 | Wason | 424/49 |
| 4,141,969 | 2/1979 | Mitchell | 424/52 |
| 4,144,321 | 3/1979 | Wason | 424/49 |
| 4,153,680 | 5/1979 | Seybert | 424/49 |
| 4,156,717 | 5/1979 | Wason | 424/49 |
| 4,159,280 | 6/1979 | Wason | 206/524.4 |
| 4,244,707 | 1/1981 | Wason | 51/308 |

*Primary Examiner*—Shep K. Rose
*Attorney, Agent, or Firm*—Lawrence S. Levinson; Burton Rodney

[57] ABSTRACT

A transparent medicated toothpaste is provided which contains amorphous silica gel in finely divided form as a polishing cleaning component combined with a saline electrolyte having a decongestive-antiedematous action. A process for preparing such toothpaste is also provided.

14 Claims, No Drawings

TRANSPARENT TOOTHPASTE HAVING A MEDICINAL ACTION AND PROCESS FOR ITS PRODUCTION

This is a continuation, of application Ser. No. 003,565, filed Jan. 15, 1979, now abandoned.

The present invention relates to a transparent toothpaste having a medicinal action and containing an amorphous silica gel in finely divided form as a polishing-cleaning component combined with a saline electrolyte having a decongestive-antiedematous action, and to a process for producing same.

In formulating a toothpaste having a medicinal action, the following criteria are considered essential:

(a) polishing-cleaning action without abrasion (scratching) of the enamel;

(b) energetic decongestive-antiedematous action associated with antibacterial and antiinflammatory activity;

(c) uniform distribution of the paste components;

(d) uniform hygroscopicity and consistency, which, as known, are essential characteristics to warrant efficacy in the therapy of the inflammatory processes of the oral mucose, and (e) non-corrosive packaging material.

In particular, a non-uniform distribution of the toothpaste components with local variations of concentration brings about the inconveniences of a further possible deterioration of the pathological condition of the oral mucose and of a reduced stability of the toothpaste.

Another drawback occurring in the preparation of toothpastes in the form of transparent gel is the introduction of salts having decongestive-antiedematous action in a therapeutically optimal quantity, without substantial alterations of the gel characteristics, in particular of its stability.

Another drawback shown by many of the toothpastes allegedly useful in the therapy of oral mucose diseases is that aluminum is generally used as the packaging material for the toothpastes. Corrosion of aluminum packages is avoided by using internal linings, which, however, increases the production cost.

It is therefore an object of the present invention to prepare a toothpaste by processing techniques which eliminate or substantially reduce the difficulties previously mentioned.

Another object is that of using saline electrolytes having a decongestive-antiedematous action, in an optimal therapeutical concentration, without impairing the characteristics and stability of the product.

Still another object is that of avoiding the drawback of corrosion of the aluminum tube, with which the toothpaste is packaged.

In order to overcome the above-mentioned difficulties, according to the present invention, a toothpaste composition whose components are all part of a single phase is prepared. In this manner, uniform distribution of the active components in the oral cavity is effected and at the same time an energetic decongestive and tonic action on the gums and a polishing-cleaning action on the tooth surface and in the interdental spaces are attained, without scratching the enamel or irritating the gums; in addition, an antibacterial action is effected which hampers the acidogenous fermentative processes of the food debris, preventing not only the formation of the bacterial plaque and of the inflammatory processes of the gums, but acting therapeutically on those already in action.

The drawback of the introduction of saline electrolytes having a decongestive-antiedematous action, is overcome by using appropriate production technology, which subsequently is described in detail and as a basic component of the toothpaste, an amorphous silica gel, in finely divided form, as described hereinafter.

Another advantage resulting from the use of a silica gel according to the present invention is that of obtaining a toothpaste having a balanced polishing-cleaning effect, so as not to induce a chemical or physical attack on the tooth enamel. The toothpaste besides, has a high degree of transparency which imparts to the product an esthetically pleasing effect.

It has now been found, in accordance with the present invention, that the above advantages can be obtained with a toothpaste comprising a single phase containing as the fundamental component an amorphous silica gel combined with a saline electrolyte, such as, for example, sodium chloride.

The amorphous silica gel which functions as a polishing-cleaning agent will preferably be in finely divided form having an average particle size ranging from 2 to 20 microns and preferably from 3 to 15 microns, with a surfacial development $\geq 300$ sq m/g and preferably from 600 to 800 sq m/g. The amorphous silica gel will comprise from about 5 to about 50% by weight of the final toothpaste composition.

The saline electrolyte will be present in an amount ranging from about 0.5 to about 20% by weight, with respect to the final toothpaste.

The amorphous silica gel will be employed in a weight ratio to the saline electrolyte of within the range of from about 1:4 to about 100:1 and preferably from about 4:1 to about 1:1.

A preferred toothpaste composition of the invention will contain from about 10 to about 18% by weight silica gel and from about 5 to about 10% by weight saline electrolyte. The preferred saline electrolyte employed in such compositions is sodium chloride.

The dentifrice compositions according to the present invention may also contain substances having a prophylactic or therapeutic action such as astringents, hydrosoluble ionic compounds of fluorine, antibacterial substances, substances having an anti-inflammatory decongestive action and filmogenes protective substances. Typical examples may be stannous fluoride, sodium monofluorophosphate, formaldehyde, organic iodine compounds, quaternary ammonium compounds, bisdiguanidines (of the type: 1,6-di-(N-p-chlorophenyl-guanidino hexane), nitroparaffin compounds (of the type: 5-amino-1,3-bis(2-ethylhexyl)-5-methylhexahydropyrimidine), natural or synthetic azulenes, 1-alpha-bisabolol, dimethylpolysiloxane, methylpolysiloxane, methylalkyl-polysiloxane and the like. The above substances may be used in amounts ranging from about 0.01 to about 2% by weight of the toothpaste composition.

The toothpaste according to the present invention, may also contain excipients such as foamers (soaps or synthetic detergents), wetting agents, preservatives, buffers, sweeteners (saccharine, ammonium glycyrrhizinate, etc.), flavoring products, dyes, opacifiers (of the type: titanium dioxide), polymeric substances and the like.

The degree of transparency of the toothpaste, according to the present invention, may be varied as a function of the composition and of the amount of the vehicular agents. Vehicular agents suitable for use herein include glycerol, sorbitol, diethylene glycol, polyethylene glycols, propylene glycol and mixtures thereof. The foregoing vehicular agents also serve as emollients.

The toothpaste of the invention may also include a binding agent such as sodium carboxymethyl cellulose, hydroxymethyl cellulose, gum tragacanth and the like and/or a thickening agent such as silica aerogel or pyrogenic silica.

A typical toothpaste in accordance with the invention has a refractive index of 1.454 at 25° C., a pH of 6.5–7.5 and a specific gravity of about 1.45 at 25° C.

In addition, in accordance with the present invention a process is provided for preparing the transparent dentifrice paste of the invention which has a medicinal action. The process of the invention includes the steps of:

(a) preparing, while in heated condition, preferably at 70°–75° C., a mixture of a binder, such as sodium carboxymethyl cellulose gel in a polyglycolic vehicle as described above;

(b) adding, while in heated condition, preferably at 80°–85° C., a saline electrolyte, preferably sodium chloride, in amounts ranging from 0.5 to 20% by weight of the entire dentifrice composition;

(c) adding after cooling, down preferably to 50°–60° C., the amorphous silica gel in amounts ranging from 5 to 50% by weight of the entire dentifrice composition, stirring unitl uniformity is attained, and (d) cooling to room temperature; and de-aerating and packaging the obtained homogeneous paste in tubes.

The process of the present invention preferably includes the following additional steps: adding sweetening and/or thickening agent and buffering agents to the mixture formed in (a) prior to the addition of saline electrolyte; prior to cooling step (c) adding foaming agents and after cooling, in step (d) adding antibacterial or similar agents, in amounts ranging from 0.01 to 2%.

In the packaging operation, aluminum tubes are employed without a protective inner lining.

By means of the above process, wherein a simple mixer may be employed, excellent dispersion of the toothpaste components is attained to produce a uniform, transparent paste, having a well defined and stable consistency with no need for a final homogenization of the product.

The following Examples represent preferred embodiments of the present invention.

EXAMPLE 1

A transparent toothpaste in accordance with the present invention having the following composition, is prepared as described below.

| Ingredient | Parts by Weight (g) |
| --- | --- |
| Polishing-cleaning compound of silica according to the present invention | 14.5 |
| Silica thickening compound | 2.5 |
| Sodium carboxymethyl cellulose | 0.5 |
| Glycerol | 5.0 |
| Sorbitol 70% solution | 45.0 |
| Polyethylene glycol 400 | 5.0 |
| Sodium saccharin | 0.2 |
| Buffer mixture | 0.89 |
| Sodium chloride | 13.0 |
| Surface active compound (sodium lauryl sulfate) | 1.5 |
| 0.5% coloring solution | 0.2 |
| Mint flavor | 1.5 |
| 1,4-Dimethyl-7-isopropylazulene | 10.0 |
| Germicide | 0.2 |
| Water | 10.0 |

5.0 g of glyceral, 45.0 g of a 70% solution of sorbitol, 5.0 g of polyethylene glycol 400 are charged into a mixer for pasty products of suitable capacity. Under fast stirring, 0.5 g of sodium carboxymethyl cellulose (high viscosity) are slowly added. The stirring is continued until dispersion is attained, then 5.0 g of deionized water containing 0.2 g of sodium saccharinate and 0.89 g of buffer mixture are added, heating slowly to 70°–75° C., always under stirring. The stirring is continued at 70°–75° C. for 45 minutes more, then heating is continued until a 80°–85° C. temperature is reached. 13 g of sodium chloride are added at this temperature and are under fast stirring, which is continued until a clear solution is obtained. 1.5 g of surface active compound (sodium lauryl sulfate) are added and, always under stirring, the mixture is slowly cooled to a temperature of 50° C. 5.0 g of deionized water containing 0.2 g of a germicide compound are added, then 2.5 g of silica thickening compound and 14.5 g of polishing-cleaning silica compound. While keeping the temperature at 50° C., the mixture is stirred slowly until a homogeneous transparent paste is obtained, then 0.2 g of coloring solution are added. The mixture is cooled down under stirring to the temperature of 30°–35° C., 1.5 g of mint flavoring and 10.0 g of 1,4-dimethyl-7-isopropylazulene are added, and the stirring is continued until homogeneity is attained. The mixture is cooled to room temperature, deaerated until a uniform, transparent paste, free from clouds and bubbles is obtained. The product is packaged in unlined aluminum tubes according to conventional techniques.

The so-prepared toothpaste is comprised of a single transparent phase and is useful in the therapy of oral mucose diseases.

The following toothpaste compositions are prepared in a manner similar to the procedure of Example 1.

| Example No. 2 | Parts by Weight |
| --- | --- |
| Polishing-cleaning compound of silica according to the present invention | 17.00 g |
| Silica thickening compound | 3.00 g |
| Sodium carboxymethyl cellulose | 1.00 g |
| Gycerol | 15.00 g |
| Sweetener | 0.21 g |
| Sodium lauryl sulfate | 2.00 g |
| Sodium chloride | 15.00 g |
| Sodium fluoride | 0.04 g |
| Preservative | 0.10 g |
| 0.5% coloring solution | 0.60 g |
| Flavor | 1.00 g |
| Water to | 100.00 g |

| Example No. 3 | Parts by Weight |
| --- | --- |
| Polishing-cleaning compound of silica according to the present invention | 13.50 g |
| Silica thickening compound | 2.00 g |
| Binder | 1.50 g |

-continued

| Example No. 3 | Parts by Weight |
| --- | --- |
| Sorbitol 70% solution | 62.58 g |
| Sodium saccharin | 0.21 g |
| Sodium lauryl sulfate | 1.00 g |
| Sodium chloride | 10.00 g |
| Perservative | 0.10 g |
| 0.5% coloring solution | 1.00 g |
| Dried extract of "Camomilla Matricaria" | 0.15 g |
| Methyl polysiloxane | 0.10 g |
| Flavor | 1.00 g |
| Water to | 100.00 g |

| Example No. 4 | |
| --- | --- |
| Polishing-cleaning compound of silica according to the present invention | 14.00 g |
| Thickening silica compound | 2.00 g |
| Hydroxyethyl cellulose | 0.50 g |
| Sorbitol: 70% solution | 51.00 g |
| Glycerol CP: 98% | 10.00 g |
| Sodium chloride | 10.00 g |
| Formaldehyde: 37% solution | 0.50 g |
| 1,4-dimethyl-7-isopropyl-azulene | 0.01 g |
| Sweetener | 0.21 g |
| Polysorbate 80 | 1.00 g |
| Coloring solution | 0.20 g |
| Flavor | 1.00 g |
| Water to | 100.00 g |

| Example No. 5 | Parts by Weight |
| --- | --- |
| Polishing-cleaning compound of silica | 15.00 g |
| Thickening compound | 3.00 g |
| Sodium carboxymethyl cellulose | 0.50 g |
| Sorbitol: 70% solution | 53.00 g |
| Polyethylene glycol | 5.00 g |
| Sodium chloride | 16.00 g |
| Cetylpyridinium chloride (germicide) | 0.20 g |
| Dried extract of "Matricaria Camomilla" | 0.15 g |
| Sodium saccharin | 0.21 g |
| Buffer mixture | 0.22 g |
| Surface active compound | 3.00 g |
| Coloring solution | 0.20 g |
| Flavor | 1.50 g |
| Water to | 100.00 g |

| Example No. 6 | |
| --- | --- |
| Polishing-cleaning compound of silica according to the present invention | 10.00 g |
| Thickening silica compound | 3.00 g |
| Hydroxypropyl cellulose | 0.50 g |
| Sorbitol: 70% solution | 60.00 g |
| Sodium chloride | 5.00 g |
| Alkyl-dimethyl-benzylammonium saccharinate | 0.10 g |
| 1-α-bisabolol | 0.20 g |
| Buffer mixture | 0.22 g |
| Surface active complex | 3.50 g |
| Coloring solution | 0.60 g |
| Flavor | 1.50 g |
| Water to | 100.00 g |

All of the above formulations are transparent, are each of a single phase and are useful in the therapy of oral mucose diseases.

I claim:

1. A process for the preparation of a toothpaste which comprises:
   (a) preparing under heat a gelled basic mass comprising a gel, and a polyglycolic vehicle;
   (b) adding to said gelled mass, while heating, de-ionized water containing buffer and then sodium chloride as a saline electrolyte in amounts ranging from 0.5 to 20% by weight of the entire toothpaste composition;
   (c) cooling said mixture from (b) and adding thereto de-ionized water, silica thickening compound and amorphous silica gel, which is in finely divided form and has an average particle size ranging from about 2 to about 20 microns and a surfacial development of within the range of from 600 to 800 $m^2/g$, in amounts ranging from 5 to 50% by weight with respect to the entire toothpaste composition, and stirring until a uniform single phase is attained, and
   (d) cooling to room temperature, deaerating until a uniform transparent paste is free from clouds and bubbles to obtain said toothpaste and packaging it in unlined aluminum tubes.

2. The process according to claim 1 wherein the temperature of the operation (a) is 70°-75° C., the temperature of the operation (b) is 80°-85° C. and that of operation (c) is 50°-60° C.

3. The process according to claim 1 characterized by the fact of adding in operation (b), before the saline electrolyte, sweetening and buffering agents, before operation (c), foaming agents, and after cooling in operation (d) antibacterial and therapeutic agents in amounts ranging from 0.01 to 2% by weight.

4. The process according to claim 1 wherein in operation (c) a thickener is added together with the amorphous silica gel.

5. The process according to claim 4 wherein said thickener is a silica aerogel or a pyrogenic silica.

6. The process according to claim 1 characterized by the fact that said gelled mass is formed of sodium carboxymethyl cellulose or hydroxymethyl cellulose in polyglycolic vehicle.

7. A transparent toothpaste composition in the form of a stable transparent gel having a refractive index equal to 1.454 at 25° C., a pH equal to 6.5 to 7.5 and a specific gravity equal to 1.45 at 25° C. having a medicinal action for the hygiene of the teeth and of the oral cavity, comprising as the essential polishing-cleaning component, a single phase comprising an amorphous silica gel in an amount ranging from about 5 to about 50% by weight of the entire toothpaste composition, said amorphous silica gel being in finely divided form and having an average particle size ranging from about 2 to about 20 microns and a surfacial development of within the range of from 600 to 800 $m^2/g$, said amorphous silica gel being uniformly combined with a decongesting-antiedematous agent comprising a saline electrolyte in an amount ranging from about 0.5 to about 20% by weight of the entire toothpaste composition, said uniform combination of amorphous silica gel and saline electrolyte forming a well-defined time-stable single aqueous phase, said single phase comprising said silica gel and saline electrolyte being uniformly distributed in a gelled basic mass, the above toothpaste having the property of being non-corrosive to unlined internal walls of aluminum tubes, produced by the process as defined in claim 1.

8. The toothpaste according to claim 7 characterized by the fact that said silica gel has an average diameter of particles ranging from about 3 to about 15 microns.

9. The toothpaste according to claim 7 wherein said amorphous silica gel is present in an amount ranging from about 10 to about 18% and said saline electrolyte is present in an amount ranging from about 5 to about 10%.

10. The toothpaste according to claim 7 further including from about 0.01 to about 2% by weight, with respect to the entire toothpaste composition, of substances having a prophylactic or therapeutic action.

11. The toothpaste according to claim 10 characterized by the fact that said substances having a prophylactic or therapeutic action are astringents, hydrosoluble ionic compounds of fluorine, antibacterials, decongestives or protective filmogenes substances.

12. The toothpaste according to claim 7 characterized by the fact that said gelled basic mass comprises a gel of sodium carboxymethyl cellulose or hydroxymethyl cellulose in a polyglycolic vehicle.

13. The toothpaste according to claim 12 wherein said polyglycolic vehicle is glycerol, sorbitol, diethylene glycol, polyethylene glycol or propylene glycol or a mixture of two or more thereof.

14. The toothpaste according to claim 7 characterized by the fact that said thickening agent is a silica aerogel or a pyrogenic silica.

* * * * *